United States Patent [19]
Jirak

[11] 3,949,758
[45] Apr. 13, 1976

[54] AUTOMATIC THRESHOLD FOLLOWING CARDIAC PACER

[75] Inventor: Thomas L. Jirak, Plymouth, Minn.

[73] Assignee: Medtronic, Inc., Minneapolis, Minn.

[22] Filed: Aug. 1, 1974

[21] Appl. No.: 493,701

[52] U.S. Cl. .................... 128/419 PG; 128/419 PT
[51] Int. Cl.² ........................................... A61N 1/36
[58] Field of Search .... 128/419 P, 419 PG, 419 PT, 128/422, 423, 421

[56] References Cited
UNITED STATES PATENTS

| | | | |
|---|---|---|---|
| 3,557,796 | 1/1971 | Keller, Jr. et al. | 128/419 PG |
| 3,618,615 | 11/1971 | Greatbatch | 128/419 PG |
| 3,669,120 | 6/1972 | Nielsen | 128/419 PG |
| 3,757,792 | 9/1973 | Mulier et al. | 128/419 PG |
| 3,805,796 | 4/1974 | Terry, Jr. et al. | 128/419 PG |

*Primary Examiner*—William E. Kamm
*Attorney, Agent, or Firm*—Lew Schwartz; Wayne A. Sivertson

[57] ABSTRACT

In a cardiac pacer including a source of timed pulses and means responsive to the timed pulses for providing controlled energy cardiac stimulating pulses, the improved apparatus including means for successively decreasing the energy of the cardiac stimulating pulses after every n pulses from the timed pulse source, n being a number greater than 1. The apparatus may also include means for increasing the energy of the cardiac stimulating pulses in the absence of a driven heartbeat and, in a preferred embodiment, may include additional apparatus to prevent loss of a heartbeat on loss of capture.

40 Claims, 5 Drawing Figures

AUTOMATIC THRESHOLD FOLLOWING CARDIAC PACER

BACKGROUND OF THE INVENTION

The minimization of cardiac pacer battery drain is a goal toward which considerable effort has been expended. For example, a major benefit of demand cardiac pacers, as opposed to asynchronous pacers, is their significant potential energy savings. Such devices sense natural heartbeats to inhibit stimulating pulses to the heart in the presence of natural heartbeats, and provide periodic stimulating pulses to the heart in the absence of natural beats. Inasmuch as the greatest battery drain results from the generation of stimulating pulses, the inhibiting of these pulses significantly reduces battery drain.

Typical prior art demand devices inherently carry high safety margins. The stimulation energy is set at an amount known to be several times that of the maximum required threshold energy in most patients. As the threshold energy of a patient is not constant, and may vary during the day, and as the threshold information is not known to the device, energy well above the expected threshold, and often maximum energy, is provided for stimulation. Obviously, this results in a high drain from the power sources and the result is shortened life time for the cardiac demand device.

A device which ameliorates the problem of high power source drain is disclosed in U.S. Pat. No. 3,757,792 of Pieter M. J. Mulier and John R. Helland issued Sept. 11, 1973 for Automatic Threshold Compensating Demand Pacemaker, which is commonly owned with the present invention. This prior art device provides for greatly decreased battery drain and thus greatly increased device lifetime by sensing each driven heartbeat and providing for a decrease in energy of each succeeding stimulating pulse until such time as no driven heartbeat occurs. When loss of capture is sensed, the next succeeding stimulating pulse is increased in energy by an amount to be safely over the threshold hysteresis level. An embodiment is also disclosed which provides an earlier extra stimulating pulse of maximum energy following loss of capture, with the following normal pulse reduced to a level only sufficiently above the threshold hysteresis level to be safe. Further stimulating pulse energy reductions occur from this reduced pulse until capture is once again lost.

By operating as described, the device of U.S. Pat. No. 3,757,792 provides for greatly decreased battery drain and thus greatly increased device lifetime. However, by decreasing the energy level of each succeeding pulse from an energy reduced pulse which itself is just above threshold, this prior art device results in frequent loss of heartbeat or, in the alternative embodiment, in frequent maximum energy pulses. For example, in the operational diagrams illustrated in FIGS. 4 and 5, every fifth stimulating pulse is below threshold which results in either a loss of heartbeat or a maximum energy stimulating pulse. Such frequent losses of heartbeat are, at the very least, disconcerting to the patient while maximum energy pulses at that same occurrence rate offset at least some of the power drain savings attending the device.

SUMMARY OF THE INVENTION

The present invention provides an apparatus which will seek or follow the patient's threshold level in a manner similar to the prior art apparatus described above while greatly reducing the heartbeat losses or maximum energy stimulating pulses within a given period of time. The apparatus of the present invention may be embodied in an R-wave responsive demand cardiac pacer. Sensing of natural and driven heartbeats are accomplished with a single sensing amplifier. Separate sensing and stimulating electrodes are preferable, each working with a third common electrode, preferably with a large enough conductive area to avoid significant polarization problems.

The output stimulation energy is controlled by a memory and output modulator. The output modulator is responsive to pulses from a clock pulse generator for providing cardiac stimulating pulses on the occurrence of each clock pulse at an energy level established by the memory. After a predetermined plurality of clock pulses, a signal is generated which alters the contents of the memory in a manner which reduces the energy level of succeeding cardiac stimulating pulses. The contents of the memory are repeatedly altered after the predetermined plurality of clock pulses to reduce the energy of the cardiac stimulating pulses and, when capture is lost, a second signal generating device again alters the contents of the memory in a manner which increases the energy of successive cardiac stimulating pulses. From this increased energy level, the contents of the memory are again repeatedly altered after a predetermined plurality of clock pulses so as to reduce the energy level of the cardiac stimulating pulses until capture is again lost. In a preferred embodiment, the stimulating pulse energy increasing signal may be applied to the memory-output modulator combination in a manner which will produce an extra increased energy stimulating pulse thereby avoiding loss of a heartbeat. In this embodiment, the apparatus also provides means for blocking the energy increasing signal from the memory when the memory contents indicate that the cardiac stimulating pulses are at a maximum desired energy.

DETAILED DESCRIPTION OF THE DRAWINGS

It should be understood that the term, "stimulating pulse" as used herein means an output pulse from the apparatus of this invention, whether or not the heart responds to the pulse. Also, the natural occurring cardiac depolarizations shall be referred to herein as a natural heartbeat while the artificially stimulated cardiac depolarizations shall be referred to as driven heartbeats, both being characterized by signals commonly referred to as QRS complexes or R waves.

Figure 1:
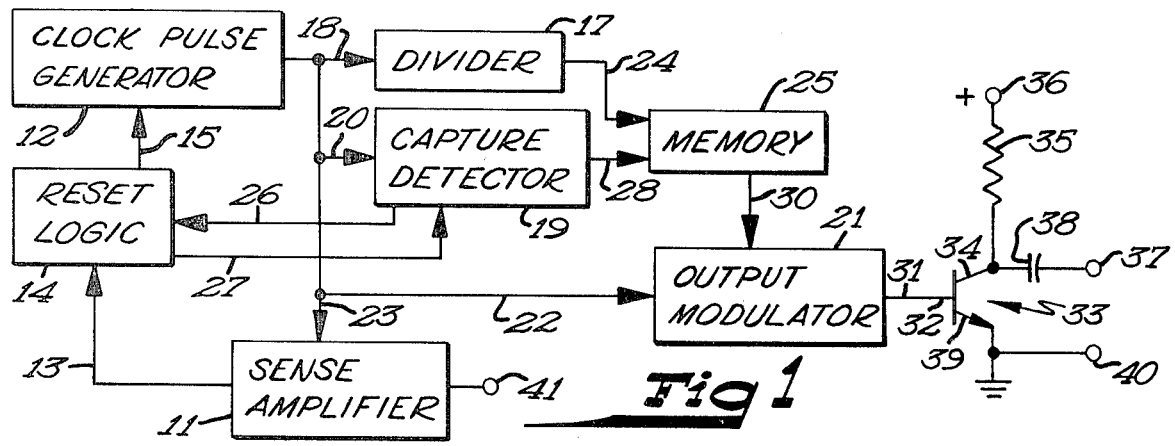
FIG. 1 is a block diagram illustrating a preferred embodiment of the present invention.

Referring first to FIG. 1, there is shown a sense amplifier 11 in block form. Amplifier 11 has the characteristics of amplifiers generally used in demand pacers which are well known to those familiar with the art, including such circuits as reversion circuits and extraneous noise or interference signal filters and preferably having a design to prevent or recover rapidly from saturation.

There is also shown in FIG. 1 a clock pulse generator 12, again shown in block form as such generators are well known to those skilled in the art. Clock pulse generator 12 includes timing means for providing periodic signal pulses, which timing means are reset when a clock pulse is provided or when a signal from sense amplifier 11 is applied to the clock pulse generator 12. As is known in the art, the signal from the sense amplifier 11 is indicative of the fact that an R-wave has been sensed from the heart.

Sense amplifier 11 is connected by a line 13 to reset logic 14. A line 15 connects the reset logic 14 to the clock pulse generator 12. Sense amplifier 11 will generate a signal on the occurrence of each natural or driven heartbeat which signal will be passed by line 13 to the reset logic 14. As will be described below, signals from sense amplifier 11 which indicate a sensing of a natural heartbeat will be passed from the reset logic 14 to the clock pulse generator 12 over the line 15. On each such signal, the clock pulse generator 12 will be reset and, if the heart continues to beat naturally at a rate greater than the rate of the clock pulse generator 12, the signal appearing on line 15 will continuously reset the generator 12 before any clock pulses are generated.

Any generated clock pulses from the clock pulse generator 12 will be applied to a divider 17 via line 18, to a capture detector 19 via line 20, to an output modulator 21 via line 22 and to the sense amplifier 11 via line 23. The divider 17 is a known device which generates an output signal after a predetermined number of input signals appear on line 18. The output signal from the divider 17 is applied via line 24 to a memory 25.

The capture detector 19 is the device which will provide the "window" during which the apparatus of FIG. 1 will sense the heart's response to a stimulating pulse. In the preferred embodiment of FIG. 1, this time is selected to be 100 milliseconds. During this window period of time, a signal from capture detector 19 will be applied to the reset logic 14 via line 26 to block any signals generated by the sense amplifier 11 from the clock pulse generator 12 and gate those signals to the capture detector 19 via line 27. The particular configuration of the reset logic 14 may take many forms and is within the skill of those familiar with the art. To repeat, during the window period of time the signal appearing on line 26 will cause the reset logic 14 to gate a signal appearing on line 13 to line 27 and capture detector 19 and block that signal from the clock pulse generator 12 and line 15. In the absence of a signal appearing on line 26, a signal appearing on line 13 will be passed by the reset logic 14 to the line 15 and the clock pulse generator 12. At the end of the window period of time the capture detector 19 will generate an end of window signal which will be passed to memory 25 via line 28.

As described above, the pulses from the clock pulse generator 12 will be applied to the output modulator 21 via a line 22 and to sense amplifier 11 via a line 23. Sense amplifier 11 contains circuitry to be described below, which will prevent the application of a signal to the line 13 during the initial portion of the window period of time established by the capture detector 19. This circuitry is activated by a pulse appearing on line 23 from clock pulse generator 12.

The memory 25 acts to control the energy of the cardiac stimulating pulses. The contents of the memory 25 are passed to the output modulator 21 via line 30. A clock pulse appearing on the line 22 acts as an enable signal to the output modulator 21 which applies a cardiac stimulating energy control signal to the line 31. The line 31 is connected to a base electrode 32 of a transistor 33. The collector 34 of transistor 33 is connected through a resistor 35 through a terminal 36 which is adapted to be connected to the positive terminal of a source of energy such as batteries and to an output electrode 37 through an output capacitor 38. The emitter electrode 39 of transistor 33 is connected to the negative terminal of the source of energy discussed above and to an output electrode 40. The electrode 37 is a stimulating electrode adapted for connection to a portion of the heart to provide stimulating pulses during the pacing mode of the apparatus of this invention. A sensing electrode 41 is similarly adapted for connection to a portion of the body, usually the heart, for sensing heartbeats in known manner while electrode 40 acts as a common electrode for both of electrodes 37 and 41 and is preferably of comparatively larger dimension to avoid polarization effects.

A signal appearing on line 31 will cause transistor 33 to turn on and apply a stimulating pulse across the electrodes 37 and 40 to stimulate the heart to which electrode 37 is connected. In the embodiment illustrated, the amplitude of the stimulating pulse will be established by the voltage applied to the terminal 36. The energy content of the stimulating pulse is regulated by operating on its pulse width which is controlled by the duration of the signal appearing on line 31. The signal on line 31 will terminate with the termination of the enable signal on line 22 and will be initiated at a time after an enable signal appears on line 22 by an amount controlled by the memory 25. Thus, by controlling the duration of the control signal on line 31, the memory 25 controls the energy of the stimulating pulses applied across the terminals 37 and 40. The memory 25 is a contents alterable memory such as a counter with the contents being altered to decrease a stimulating pulse duration upon the occurrence of a signal on line 24 and to increase the duration of the stimulating pulses upon the occurrence of a signal on line 28.

The cardiac depolarization response of a heartbeat is known to those familiar with the art. For example, in FIG. 3 of U.S. Pat. No. 3,757,792, which is hereby incorporated by reference, there is shown a one millisecond stimulating pulse followed by the QRS complex from the heart. As stated in the incorporated patent, the QRS complex occurs within approximately 15 milliseconds after the stimulating pulse, and the R-wave occurs within approximately 75 milliseconds after the stimulating pulse. The T-wave does not occur until approximately 210 milliseconds after the stimulating pulse. It is the QRS complex that the apparatus of FIG. 1 wishes to sense to determine when the heart has not responded, during the window time, to the stimulation pulse provided between the electrodes 37 and 40.

As is known to those familiar to the art, the timing of the waves forming the QRS complex will vary from patient to patient, and may vary within the patient himself. It has been experimentally shown, and is generally accepted by those familiar with the art, that the R-wave will be completed in virtually all patients within 100 milliseconds after the stimulating pulse. It is for this reason that the window has been chosen at that length for the preferred embodiment. It is also generally known from experiments that stimulation artifacts may occur during the first 10 to 20 milliseconds after the stimulating pulse. Because such an artifact may cause a pulse to appear from the amplifier 11, amplifier 11 is provided with circuitry which will prevent it from generating a signal during the first 20 milliseconds after the stimulating pulse. This, in effect, makes the effective portion of the window the last 80 milliseconds of the window period of time. The period of the clock pulse generator may be 800 milliseconds, for example.

In operation, and assuming natural heartbeat action at a rate faster than 75 beats per minute, the sense amplifier 11 will sense a natural heartbeat through its sensing electrode 41 within the 800 millisecond time period of the clock generator 12. The sensed heartbeat will reset the clock generator 12 through the action of the reset signal transmitted from sense amplifier 11 via line 13, reset logic 14 and line 15. Should a heartbeat fail to occur within the 800 millisecond time period of the clock pulse generator 12, a clock pulse will be generated and applied to the divider 17, capture detector 19, output modulator 21 and sense amplifier 11. As described above, this will cause the output from the sense amplifier 11 to be disabled for 20 milliseconds while the 100 millisecond window signal will be applied to the reset logic 14 over the line 26 causing any output signals from the sense amplifier 11 to be gated to the capture detector 19. Also, the pulse from the clock pulse generator 12 will act as an enable signal to the output modulator 21 thereby producing a controlled energy cardiac stimulating pulse across the electrodes 37 and 40. If a driven heartbeat is detected by the sense amplifier 11, the sense amplifier reset signal on line 13 will be gated to line 27 to reset the capture detector and prevent the generation of the end of window signal over the line 28. Assuming that the stimulating pulse is above the patient's threshold level and no natural heartbeat occurs to reset the clock pulse generator 12, a series of stimulating pulses of equal energy will be applied to the heart across the electrodes 37 and 40. After a predetermined number of such pulses, the divider 17 will apply a signal to the memory 25 via the line 24. This signal will alter the contents of the memory and result in a decrease in the energy of the stimulating pulses. The stimulating pulses will continue at this decreased level until an identical number of clock pulses have been generated by the clock pulse generator 12 thereby causing the divider 17 to generate another memory content altering signal. In this manner, the energy content of the stimulating pulses will be continually decreased after every predetermined plurality of clock pulses until their energy is below the threshold level and capture is lost. Upon loss of capture, no reset signal from sense amplifier 11 will be applied to the capture detector 19 and thus, the end of window signal from capture detector 19 will be applied to the memory 25 via the line 28. The end of window signal on line 28 will alter the contents of the memory 25 thereby increasing the energy of the stimulating pulses succeeding the single pulse which fell below the threshold level. Again in the absence of natural heartbeat, the energy of successive stimulating pulses will be decreased under the control of the divider 17 and memory 25 until such time as capture is again lost and the contents of the memory is again altered to increase the energy of the stimulating pulses.

It is apparent that the energy of the stimulating pulses in the apparatus of FIG. 1 will seek and follow the threshold level of the patient while losing capture less often than the apparatus of the incorporated patent. For example, if the divider 17 generates a signal on each 16th clock pulse, there will be 15 stimulating pulses at the same energy level with the 16th pulse having a reduced energy through the action of the divider output signal on memory 25. If this reduced energy is below the threshold level, the end of window signal on line 28 will cause the memory 25 to increase the energy of the stimulating pulses to a level above threshold with that level being maintained until another divider output signal is provided. Thus, the apparatus of the present invention preserves the energy savings of the incorporated prior art device while ameliorating the effects of a frequent loss of capture inherent in that device. In an implantable device, it may be convenient to generate a divider output signal every 256 clock pulses. Of course, the divider output may be generated after any number of clock pulses with any power of two being convenient in the digital embodiments to be described below. In an external device, it may be convenient to generate a divider signal after fewer clock pulses. Such external devices would typically be temporary for the purpose of measuring threshold with the frequency of a heartbeat loss being less significant. A convenient number of clock pulses per divider signal for an external device may be 16, for example.

Figure 2:
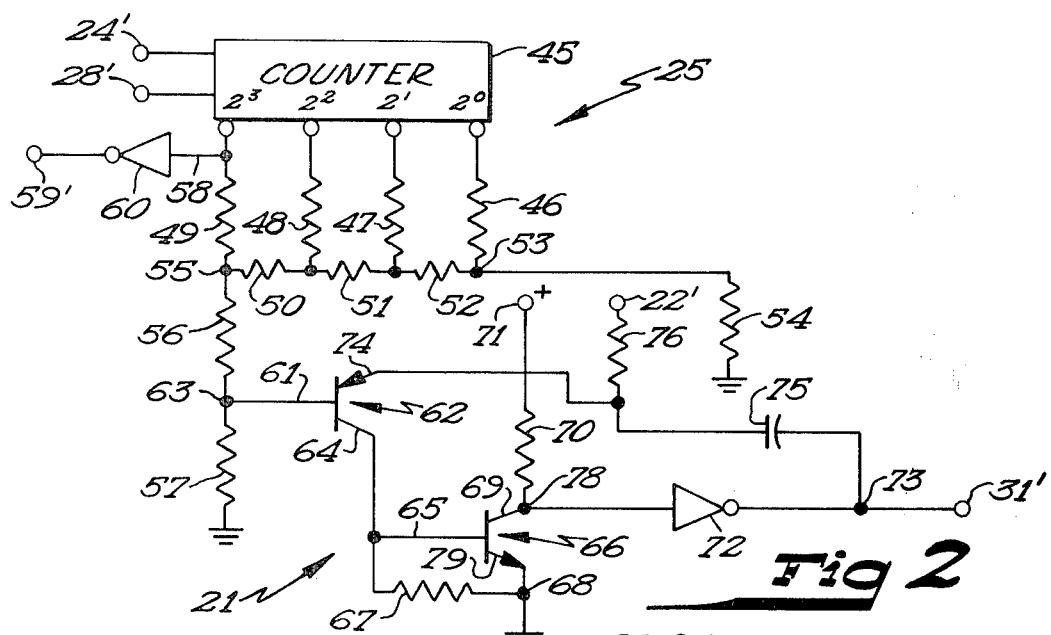
FIG. 2 is a schematic diagram illustrating a portion of the preferred embodiment of FIG. 1.

Referring now to FIG. 2, there is shown a schematic of a preferred form of the memory 25 and output modulator 21 of FIG. 1. The memory 25 is composed of a counter 45 shown here as a bidirectional binary counter having outputs representing 1, 2, 4 and 8, as is known to those familiar with the art. Each of the outputs of the counter is inverted and connected to a ladder network consisting of resistances 46–52. The junction 53 between resistances 46 and 52 is connected to ground by a resistance 54 and a junction 55 between resistance 49 and 50 is connected to ground by resistances 56 and 57. Typically, the resistances 46–49 and 54 have a resistance twice the resistance of the resistors 50–52 and may conveniently have a resistance of 200 K ohms. In the configuration shown in FIG. 2, the voltage at the junction 55 will go down as the count in the counter goes up and vice versa. The lines 58 and 59 and the inverter 60 will be discussed more fully with reference to the embodiment of FIG. 5.

The resistances 56 and 57 form a voltage divider to which the base electrode 61 of a transistor 62 is connected at a junction 63. The collector electrode 64 of transistor 62 is connected to the base electrode 65 of a transistor 66 and through a resistor 67 to a grounded junction 68. The collector electrode 69 of transistor 66 is connected, at junction 78, through a resistor 70 to the positive terminal 71 of a source of energy such as batteries and through an inverter 72 to a junction 73. The emitter electrode 74 of transistor 62 is connected to the junction 73 by a capacitor 75 and to a terminal 22' by a resistor 76. The emitter electrode 79 of transistor 66 is connected to terminal 68.

The counter 45 is provided with terminals 24' and 28'. Upon the occurence of a signal at the terminal 24', the count in the counter will decrease by 1 while a signal appearing at the terminal 28 will cause an increase of 1 in the count of the counter. Alternatively, a signal appearing at the terminal 28' may cause the count in the counter to go to a preselected value, the manner by which the count in the counter is increased or decreased through signals appearing at the terminals 24' and 28' being known to those familiar with the art. Throughout this specification the primed and double primed terminals are intended to be connected to the identically numbered interconnecting lines.

In operation, a clock pulse appearing at terminal 22' will cause the capacitor 75 to begin charging. When the charge on the capacitor is sufficient, the transistor 62 will turn on which will, in turn, turn on transistor 66 bringing the junction 78 to ground potential. This potential will be inverted by the inverter 72 thus producing a positive pulse at the junction 73 and at terminal 31'. The positive pulse will terminate with the termination of the clock pulse applied to the terminal 22'. The duration of the pulse at the terminal 31' is dependent upon the duration of the clock pulse at the terminal 22' and the count in the counter. For example, the count in the counter is transformed to a voltage at junction 55 which is applied to the base electrode 61 of the transistor 62 through the voltage dividing resistors 56 and 57. As the count in the counter increases, the voltage at the junction 55, and thus the junction 63, decreases requiring less charge on the capacitor 75 to turn on the transistor 62. Thus, the higher the count in the counter, the shorter the delay between the appearance of a clock pulse at the terminal 22' and the turn on of the transistor 62 and appearance of stimulating energy control pulse at the terminal 31'. While the duration of the stimulating energy control pulse at the terminal 31' is dependent upon the duration of the clock pulse at the terminal 22' and the count in the counter, with clock pulses of uniform duration the duration of the stimulating energy control pulses at the terminal 31' is dependent upon the count in the counter and will increase following the application of a signal to the terminal 28' and will decrease following a signal applied to the terminal 24'.

Figure 3:
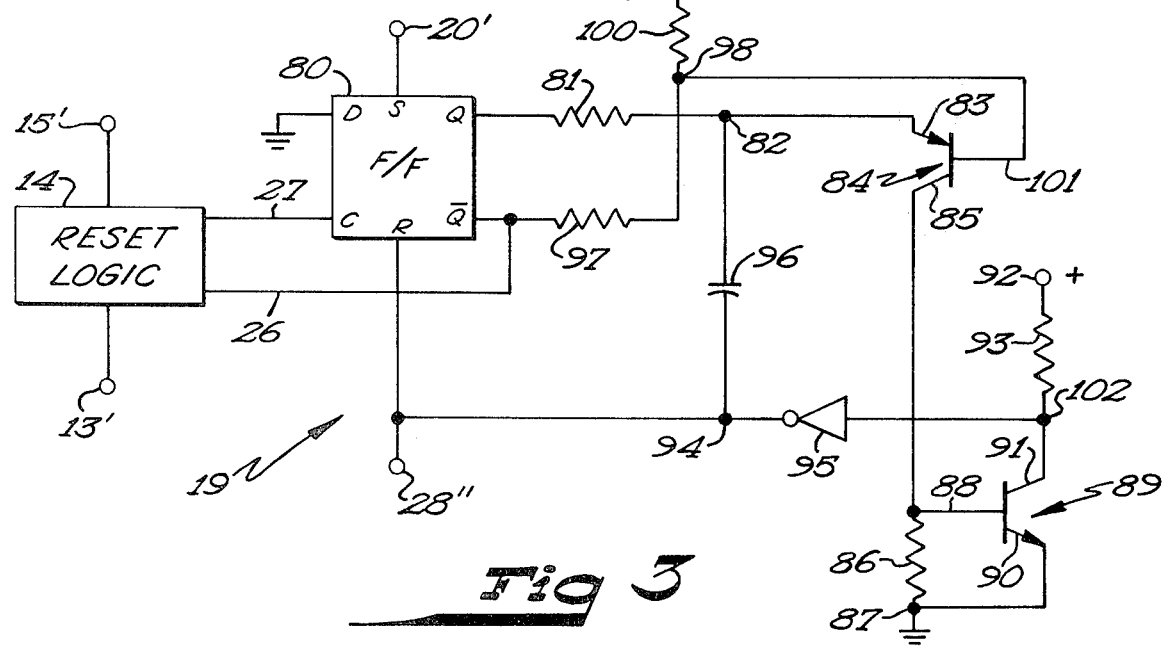
FIG. 3 is a schematic diagram showing a portion of the preferred embodiment of FIG. 1.

Referring now to FIG. 3, there is shown a schematic of a preferred form of a capture detector 19 of FIG. 1. A D type flip-flop 80 has its set terminals connected to a terminal 20' which is adapted for connection to line 20 of FIG. 1. The clock terminal C of flip-flop 80 is connected to the reset logic 14 by the line 27 and the inverted output $\bar{Q}$ terminal of the flip-flop 80 is connected to the reset logic 14 by the line 26. Reset logic 14 has a terminal 13' adapted for connection to the line 13 and a terminal 15' adapted for connection to the line 15. The input terminal D of flip-flop 80 is connected to ground and its output terminal Q is connected through a resistor 81 to a junction 82. The reset terminal R of flip-flop 80 is connected to junction 94 and terminal 28". Junction 82 is connected to the emitter electrode 83 of a transistor 84. The collector electrode 85 of transistor 84 is connected to the base electrode 88 of transistor 89 and to a grounded junction 87 through a resistance 86. The emitter electrode 90 of transistor 89 is connected to the junction 87 while its collector electrode 91 is connected to a terminal 92 through a resistance 93 and to the junction 94 and the terminal 28" through an inverter 95. A capacitor 96 connects the junctions 82 and 94. The $\bar{Q}$ terminal of flip-flop 80 is connected through a resistance 97 to a junction 98, the junction 98 being connected to a terminal 99 through a resistance 100 and to the base electrode 101 of transistor 84. The terminals 92 and 99 are adapted to be connected to a positive terminal of the source of energy such as batteries.

In operation, a clock pulse appearing at the terminal 20' will set the flip-flop 80 in known manner. When the flip-flop 80 is set by the appearance of a clock pulse at the terminal 20', the Q terminal of flip-flop 80 will be high and the $\bar{Q}$ terminal will be low. When the Q terminal of flip-flop 80 goes high, the capacitor 96 will begin to charge and will turn on the transistor 84 after a period of time established by the resistance 81 and the capacitance of capacitor 96. Turn on of the transistor 84 will turn on the transistor 89 which will bring the junction 102 to ground. The signal at junction 102 is inverted by the inverter 95 to provide a reset signal at the R terminal of flip-flop 80 and an output signal at the terminal 28". The reset signal of the flip-flop 80 will switch its outputs such that the Q output is low and the $\bar{Q}$ output is high. The capacitor 96 will maintain the transistor 84 in the "on" state until the capacitor 96 discharges sufficiently through the resistor 81 and transistor 84 to allow the transistor 84 to turn off.

From the above, it can be seen that a clock pulse appearing at terminal 20' will cause a change of state of the Q and $\bar{Q}$ terminals of flip-flop 80 with that state being maintained for a period of time established by the resistor 81 and capacitance 96. That period of time is the window period of time during which signals appearing on line 13 in FIG. 1 are at least blocked from the clock pulse generator 12 by the reset logic 14. It is apparent that either the Q or $\bar{Q}$ signal may be employed by the reset logic 14 to establish the window period of time. Also, during the window period of time, a signal appearing at the terminal 13' will be gated by the reset logic 14 over the line 27 to the C terminal of flip-flop 80 thereby causing the Q terminal to go low and stop the charging of the capacitor 96 prior to turn on of the transistors 84 and 89. In this way, the end of window signal at terminal 28" is inhibited. Clearly, in the embodiment of FIG. 3, the signal appearing at the terminal 13' can be applied directly to the C terminal of flip-flop 80 as opposed to being gated through the reset logic 14.

Figure 4:
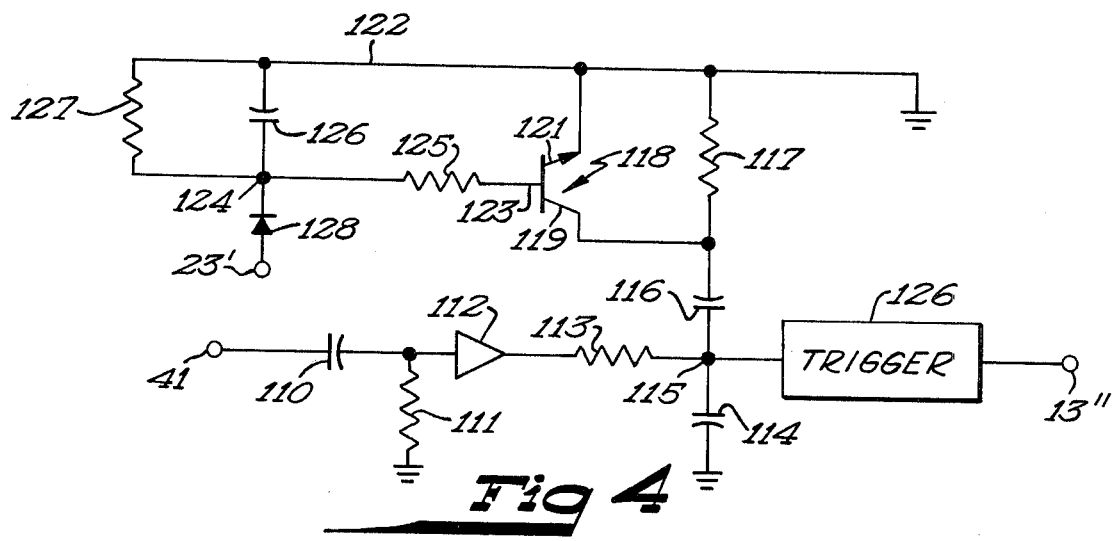
FIG. 4 is a schematic diagram showing a portion of the preferred embodiment of FIG. 1.

FIG. 4 illustrates, in schematic diagram, a preferred form of the sense amplifier 11 of FIG. 1. A terminal 41 is connected through a filter composed of a capacitance 110 and grounded resistance 111 to an amplifier 112. The amplifier 112 is of a type known to those familar with the art having a fast recovery and high frequency response. The amplifier 112 is connected through another filter composed of a resistance 113 and grounded capacitance 114 which are connected at their junction 115 to a trigger circuit 116. The amplifier circuitry discussed to this point is conventional and is well known to those familiar with the art for applying a signal to the terminal 13" in response to a signal sensed at the electrode 41.

Connected to the junction 115 is an analog gate composed of capacitance 116 and resistance 117. Connected across resistance 117 is a transistor 118 whose collector electrode 119 is connected to a junction 120 between the resistance 117 and capacitance 116. The emitter electrode 121 of transistor 118 is connected to a negative bus 122 and the base electrde 123 of transistor 118 is connected to a junction 124 via a resistor 125. A capacitor 126 and a resistance 127 are connected between the negative bus 122 and the junction 124. A diode 128 connects the terminal 23' to the junction 124.

In operation, and assuming no clock pulse has been applied to the terminal 23', a heartbeat sensed by the sensing electrode 41 will result in a reset signal being applied to the terminal 13''. Upon the occurrence of a clock pulse at terminal 23', the capacitor 126 will charge and turn on the transistor 118. For the purposes of the present invention, the on time of the transistor 118 is intended to be 20 milliseconds during which time the resistance 117 is shorted. Also, during this 20 millisecond period the capacitance 116 may be treated as a short and any signals appearing at the junction 115 will be shunted away from the trigger 126 thereby preventing the generation of a reset signal at the terminal 13''. The values of the capacitance 116 and resistance 117 are selected to be sufficiently greater than the values of the capacitance 115 and resistance 113 so that their effect on the amplifier is virtually negligible during the time that the transistor 118 is off.

The embodiment of FIG. 1, including the preferred form of its various components as described with references to FIGS. 2, 3, and 4, will seek and follow a patient's threshold in a manner similar to that of the apparatus of the incorporated patent. However, the apparatus of the present invention does not have the frequent loss of heartbeat or maximum energy stimulating pulse of that prior art apparatus. Thus, the apparatus of the present invention provides the energy saving advantages of the incorporated prior art apparatus while greatly ameliorating the difficulties attending the frequency of stimulating pulses below the threshold level. In the embodiment of FIG. 1, it may be desirable after capture is lost, to increase the energy of the stimulating pulses to a level greater than the energy of the stimulating pulses immediately preceding lost of capture. For this purpose, the signal appearing at the terminal 28' (see FIG. 2) may set the counter to a predetermined count, in a manner known to those familiar with the art, as opposed to merely increasing the count in the counter by 1. Indeed, the hysteresis effect found in many patients may require this type of operation. For example, it is commonly accepted that once stimulation had dropped below the stimulus threshold level of the patient, to regain capture it is necessary to raise the stimulus voltage to a point above the level at which capture was lost. In the embodiment of FIG. 1, an increase in stimulation energy resulting from an increase in the counter of 1 may be insufficient to overcome this hysteresis effect while an increase to a predetermined count can be confidently relied upon to provide stimulating pulses at an energy which will regain capture.

As an alternative to significantly increasing the count of the counter to overcome the hysteresis effect, it is possible to obtain and maintain capture by generating a single pulse of relatively greater energy followed by a series of pulses just above threshold. In the apparatus of the incorporated patent, this approach is utilized in a form of a maximum energy pulse following loss of capture followed by a series of successively lower energy pulses from a level below the maximum level. This same general approach can be accomplished in a modified form of the present invention in a manner which is also more energy conserving than the apparatus of the incorporated patent. In addition, this modified version of the present invention may detect a malfunction of the capture detector and continue to provide stimulating pulses at an energy sufficient to insure capture.

Figure 5:
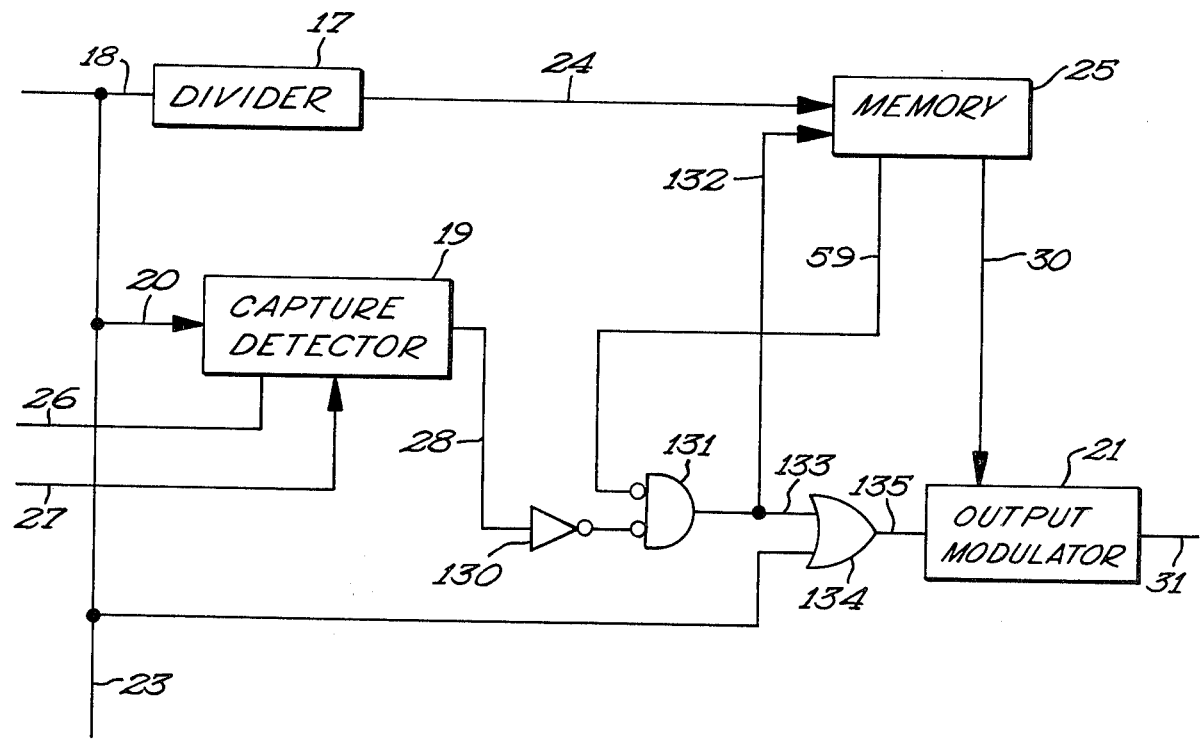
FIG. 5 is a block diagram of a portion of FIG. 1 showing components added to make a second embodiment of the present invention.

Referring now to FIG. 5 there is shown the modification of the present invention discussed above. In FIG. 5, like reference numerals indicate components which are functionally identical to those of the embodiment of FIG. 1. For example, a divider 17 receives clock pulses from the line 18 and applied a stimulation pulse energy decreasing signal to the memory 25 over the line 24. In the counter embodiment of the memory 25 illustrated in FIG. 2, the signal appearing on line 24 is a counter decrementing signal. Similarly, the contents of the memory (counter) 25 is applied to the output modulator 21 over the line 30. Generation, by the capture detector 19, of a window signal on line 26 and an end of window signal on line 28 is similarly unaffected as is the resetting of the capture detector 19 by a signal appearing on the line 27. In the embodiment of FIG. 5, the end of window signal on line 28 is inverted by inverter 130 and is applied to an input of gate 131. Gate 131 is illustrated as an AND gate having inverted inputs and functions as a NOR gate. The signal appearing at the terminal 59' (see FIG. 2) is applied as the other input to gate 131. The output of the gate 131 is applied to the memory 25 via a line 132, the signal on line 132 functioning in a manner identical to the memory input on line 28 in the embodiment of FIG. 1. The output of the gate 131 is also applied by a line 133 to an OR gate 134 whose output is connected to output modulator 21 via a line 135. The clock pulses appearing on line 22 operate as an input to the OR gate 134 in the embodiment of FIG. 5 as opposed to a direct input to the output modulator 21 in the embodiment of FIG. 1.

In the modified embodiment of FIG. 5 the maximum desired energy of the stimulating pulses is represented by a predetermined count in the counter of FIG. 2, a count of 8, for example. When the count of the counter is 8, the terminal 59' will be high and the input on line 59 to the NOR gate 131 will similarly be high. In this state, the end of window signal on line 28, inverted by inverter 130, will be blocked at the gate 131 by the high signal appearing on line 59. Thus, the memory (counter) 25 will not be incremented to increase the energy of the stimulating pulses inasmuch as no incrementing signal will appear on line 132. In this manner, with the memory 25 already providing the maximum desired energy in the stimulating pulses, the failure of the capture detector 19 to detect a driven heartbeat during the window period of time will not cause an increase in the energy of successive stimulating pulses, but instead, the next stimulating pulse will be at the same maximum desired level and will occur upon the next clock pulse. It must be pointed out that this particular condition most likely indicates a malfunction of the capture detector 19 in which case it is obviously desirable to maintain succeeding stimulating pulses independent of any control from the capture detector 19.

Assuming a count in the counter less than 8, the signal appearing on line 59 will be low and the end of window signal on line 28, inverted by inverter 130, will produce a high output from gate 131 which will cause the count in the memory 25 to be incremented through application of the signal through the line 132 and will generate an extra stimulating pulse through the application of the signal from the gate 131 to the output modulator 21 through the line 133, OR gate 134 and line 135. Inasmuch as the signal on line 28 results from the fact that capture has been lost, it is desirable that a stimulating pulse resulting from a signal on line 133 have an energy content sufficient to re-establish capture. As discussed above, this may require that the stimulating pulses have an energy greater than that attained by merely incrementing the counter by 1. Thus, unless the signal on line 132 increments the counter by more than 1 or presets the counter to a higher predetermined count, before the extra stimulating pulse, the stimulating pulse enabled by the signal on line 133 may be insufficient to re-establish capture. However, inasmuch as the stimulating pulse energy control signal on line 31 is dependent upon the count in the counter and duration of the enable signal, if the enable signal resulting from the end of the window signal on line 28 has a longer duration than the clock pulses appearing on line 22 the stimulating energy control pulse on line 31 will result in a stimulation pulse of greater energy than it would otherwise have under control of the memory and the clock pulse. Thus, by operating on the capture detector in a manner which will provide an end of window signal of greater duration than the clock pulse signal the stimulating pulse resulting from the end of window signal on line 28 has sufficient energy to reestablish capture thus allowing successive stimulating pulses under the control of the memory 25 and clock pulses at a level just above threshold. It is apparent in the embodiment of FIG. 3, that the duration of the signals on line 28 may be controlled by the discharge time of capacitor 96 which may be established in known manner.

The present invention provides a new and novel apparatus which will seek and follow a patient's threshold so as to minimize battery drain while ameliorating the difficulties attending the known prior art device resulting from frequent loss of heartbeat or maximum energy stimulating pulses. Additionally, the apparatus of the present invention may be constructed largely from digital components which provide a greater stability of operation inasmuch as these components are not as subject to parameter variations or changes in leakages as are analog devices such as the apparatus of the incorporated patent. Also, the digital components require no calibration and may be tested on a "go/no-go" basis. The apparatus of the present invention may be constructed to provide any number of stimulating pulses at each energy level and may be operated with as many energy level steps from maximum and minimum energy as is desired. It is contemplated that a device built according to the present invention may have eight or 16 energy levels between maximum and minimum energy and will provide 256 stimulating pulses at each energy level before the energy level is decreased. In an external device it may be desirable to use fewer stimulating pulses at each energy level and more energy levels. Finally, it must be pointed out that the potential for constructing the present invention from digital components would provide a device greatly reduced in size which, in an implantable mode, is a highly desirable feature.

Obviously many modifications and variations of the present invention are possible in light of the above teachings. It is therefore to be understood that, within the scope of the appended claims, the invention may be practiced otherwise than as specifically described.

What is claimed is:

1. In a cardiac pacer of the type having a source of timed pulses and having means for providing energy controlled cardiac stimulating pulses in response to pulses from said timed pulse source, the improvement comprising:
   said means for providing energy controlled cardiac stimulating pulses including means connected and responsive to said timed pulse source for decreasing the energy of successive cardiac stimulating pulses only after every $n$ pulses from said timed pulse source, $n$ being a number greater than 1, and further including means for increasing the energy of successive cardiac stimulating pulses in the absence of a driven heartbeat.

2. The apparatus of claim 1 wherein said stimulating pulse energy decreasing means comprises means for generating a signal after n pulses from said timed pulse source, said stimulating pulse energy increasing means comprising means for generating a signal a predetermined time after each of said timed pulses and including means for inhibiting said increasing means signal on the occurrence of a driven heartbeat.

3. The apparatus of claim 2 wherein said means for providing energy controlled cardiac stimulating pulses comprises counter means whose count is altered in one direction in response to said energy decreasing means signal and in the other direction in response to said energy increasing means signal, said means for providing energy controlled cardiac stimulating pulses further comprising means responsive to the count in said counter means and said timed pulse source pulses for providing a stimulating energy control pulse upon the occurrence of each pulse from said timed pulse source.

4. In a demand cardiac pacer of the type having a source of timed pulses, means for inhibiting said timed pulse source in response to a natural heartbeat and means for providing energy controlled cardiac stimulating pulses in response to said timed pulse source pulses, the improvement comprising:
   first means connected and responsive to said timed pulse source for generating a signal only after $n$ pulses from said timed pulse source, $n$ being a number greater than 1;
   second means connected to said timed pulse source for generating a signal a predetermined time following a pulse from said timed pulse source; and
   means for inhibiting said second means in response to a driven heartbeat;
   said means for providing energy controlled cardiac stimulating pulses including means responsive to said first and second means for decreasing the energy of successive cardiac stimulating pulses upon the occurrence of said first means signal and increasing the energy of successive cardiac stimulating pulses upon the occurrence of said second means signal.

5. The apparatus of claim 4 wherein the means for inhibiting the timed pulse source and the means for inhibiting the second means comprise single sense amplifier means adapted to be connected to the heart to detect natural and driven heartbeats and reset logic means connected to said sense amplifier means and interconnecting said timed pulse source and said second means with said sense amplifier means for selectively blocking an inhibit signal from said sense amplifier means from at least one of said timed pulse source and said second means.

6. The apparatus of claim 5 wherein said sense amplifier inhibit signal is blocked from said timed pulse source during the interval between a pulse from said timed pulse source and said second means signal.

7. The apparatus of claim 5 wherein said sense amplifier means is connected to said timed pulse source and comprises means for blocking said sense amplifier means inhibit signal for a predetermined time following each pulse from said timed pulse source.

8. The apparatus of claim 5 wherein said blocking means comprises gate means for gating said sense amplifier means inhibit signal to one or the other of said timed pulse source and said second means.

9. The apparatus of claim 8 wherein said sense amplifier inhibit signal is gated to said second means during the interval between a pulse and said second means.

10. The apparatus of claim 9 wherein said sense amplifier means is connected to said timed pulse source and comprises means for blocking said sense amplifier means inhibit signal for a predetermined time following each pulse from said timed pulse source.

11. The apparatus of claim 4 wherein the means responsive to the first and second means comprises counter means whose count is altered in one direction by said first means signal and in the other direction by said second means signal, said means for providing energy controlled cardiac stimulating pulses further comprising means responsive to the count in said counter means and the pulses from said timed pulse source for providing a stimulating energy control pulse upon the occurrence of each pulse from said timed pulse source, the energy content of each stimulating energy control pulse being dependent on the count in said counter means.

12. The apparatus of claim 11 further comprising means for preventing the alteration of the count in said counter means by said second means signal when the count in said counter means is at a predetermined value.

13. The apparatus of claim 11 wherein said means for providing energy controlled cardiac stimulating pulses comprises means responsive to the signal from said second means and the count in said counter means for providing an extra stimulating energy control pulse.

14. The apparatus of claim 13 further comprising means for blocking said second means signal when the count in said counter means is at a predetermined value.

15. The apparatus of claim 13 further comprising means for blocking said second means signal when the count in said counter means is at a predetermined value.

16. The apparatus of claim 15 wherein said sense amplifier means is connected to said timed pulse source and comprises means for blocking said sense amplifier means inhibit signal for a predetermined time following each pulse from said timed pulse source.

17. The apparatus of claim 11 wherein said first means comprises means for successively generating a signal after every n pulses from said tuned pulse source.

18. The apparatus of claim 17 wherein the means for inhibiting the timed pulse source and the means for inhibiting the second means comprise single sense amplifier means adapted to be connected to the heart to detect natural and driven heartbeats and reset logic means connected to said sense amplifier means and interconnecting said timed pulse source and said second means with said sense amplifier means for selectively blocking an inhibit signal from said sense amplifier means from at least one of said timed pulse source and said second means.

19. The apparatus of claim 18 wherein said means for providing energy controlled cardiac stimulating pulses comprises means responsive to the signal from said second means and the count in said counter means for providing an extra stimulating energy control pulse.

20. A demand cardiac pacer which comprises:
resettable clock pulse generator means;
sense amplifier means adapted to be connected to a heart for providing a reset signal in response to a heartbeat;
means connected and responsive to said clock pulse generator means for providing an alter signal only after n pulses from said clock pulse generator means, n being a number greater than 1;
window timing means for establishing a limited window period of time following each pulse from said clock pulse generator;
means interconnecting said clock pulse generator means and said sense amplifier means and responsive to said window timing means for blocking said reset signal from said clock pulse generator means during said window period of time; and
means for providing energy controlled cardiac stimulating pulses including output means adapted to be connected to a heart, said stimulating pulse means including contents alterable memory means for controlling the energy of each stimulating pulse in accordance with the contents thereof and enable means responsive to pulses from said clock pulse generator for applying controlled energy control pulses to said output means, said contents alterable memory means being connected to said alter signal providing means for altering the contents of said memory means in response to said alter signal.

21. The apparatus of claim 20 wherein said sense amplifier means is connected to the output of said clock pulse generator means and comprises means for blocking said reset signal for a predetermined time following a pulse from said clock pulse generator means.

22. The apparatus of claim 20 wherein said window timing means further comprises means for generating a window end signal after said limited window period of time, said contents alterable memory means being connected to said window timing means for increasing the energy of stimulating pulses following said window end signal.

23. The apparatus of claim 22 wherein said window end signal generating means comprises means connected to said sense amplifier means for inhibiting said window end signal generating means in response to said reset signal.

24. The apparatus of claim 20 wherein said contents alterable memory means comprises counter means, the count in said counter means being altered in one direction in response to said alter signal.

25. The apparatus of claim 24 wherein said counter means comprises binary counter means, the outputs of said binary counter means being connected to ladder network means.

26. The apparatus of claim 25 wherein said enable means comprises control pulse timing means connected to said ladder means and responsive to pulses from said clock pulse generator means for generating control pulses of a duration less than the duration of the pulses from said clock pulse generator means.

27. The apparatus of claim 26 wherein said window timing means further comprises means for generating a window end signal after said limited window period of time, the count in said counter means being altered in the other direction in response to said window end signal.

28. The apparatus of claim 27 wherein said control pulse timing means is responsive to said window end signal for generating pulses of a duration less than the duration of said window end signal.

29. The apparatus of claim 28 wherein said window end signal generating means comprises means connected to said sense amplifier means for inhibiting said window end signal generating means in response to said reset signal.

30. The apparatus of claim 29 further comprising means for blocking said window end signal when said counter is at a predetermined count.

31. The apparatus of claim 20 wherein said window timing means further comprises means for generating a window end signal after said limited window period of time, said contents alterable memory means being connected to said window timing means for increasing the energy of stimulating pulses following said window end signal.

32. The apparatus of claim 31 wherein said contents alterable memory means comprises counter means, the count in said counter means being altered in one direction by said alter signal and in the other direction by said window end signal.

33. The apparatus of claim 32 wherein said alter signal providing means comprises means for providing an alter signal after every $n$ pulses from said clock pulse generator means.

34. The apparatus of claim 32 further comprising means for blocking said window end signal from said counter means when said counter means is at a predetermined count.

35. The apparatus of claim 31 wherein said enable means is responsive to said window end signal for applying extra control pulses to said output means.

36. The apparatus of claim 35 wherein said blocking means blocks said window end signal from said enable means when said counter means is at a predetermined count.

37. The apparatus of claim 35 wherein said contents alterable memory means comprises counter means, the count in said counter means being altered in one direction by said alter signal and in the other direction by said window end signal.

38. The apparatus of claim 37 further comprising means for blocking said window end signal from said counter means and said enable means when the said counter is at a predetermined count.

39. The apparatus of claim 37 wherein said alter signal providing means comprises means for providing an alter signal after every $n$ pulses from said clock pulse generator means.

40. The apparatus of claim 20 wherein said alter signal providing means comprises means for providing an alter signal after every $n$ pulses from said clock pulse generator means.

* * * * *